(12) United States Patent
Sperl et al.

(10) Patent No.: US 11,530,987 B2
(45) Date of Patent: Dec. 20, 2022

(54) PHOTONIC GAS SENSOR AND METHOD FOR PRODUCING A PHOTONIC GAS SENSOR

(71) Applicant: OSRAM OLED GmbH, Regensburg (DE)

(72) Inventors: Matthias Sperl, Mintraching (DE); Tim Boescke, Regensburg (DE); Daniele Brunazzo, Regensburg (DE)

(73) Assignee: OSRAM OLED GMBH, Regensburg (DE)

( * ) Notice: Subject to any disclaimer, the term of this patent is extended or adjusted under 35 U.S.C. 154(b) by 152 days.

(21) Appl. No.: 16/763,923

(22) PCT Filed: Nov. 23, 2018

(86) PCT No.: PCT/EP2018/082390
§ 371 (c)(1),
(2) Date: May 13, 2020

(87) PCT Pub. No.: WO2019/101933
PCT Pub. Date: May 31, 2019

(65) Prior Publication Data
US 2020/0363335 A1    Nov. 19, 2020

(30) Foreign Application Priority Data
Nov. 23, 2017 (DE) .......................... 102017127671.8

(51) Int. Cl.
*G01N 21/64* (2006.01)
*G01N 33/00* (2006.01)

(52) U.S. Cl.
CPC ....... *G01N 21/6428* (2013.01); *G01N 33/004* (2013.01); *G01N 33/0037* (2013.01);
(Continued)

(58) Field of Classification Search
CPC .......... G01N 21/6428; G01N 33/0037; G01N 33/004; G01N 33/0054; G01N 2021/6439;
(Continued)

(56) References Cited

U.S. PATENT DOCUMENTS

| 2006/0285114 | A1* | 12/2006 | Cao | G01N 21/3504 356/440 |
| 2011/0171067 | A1* | 7/2011 | Mueller | G01N 21/6428 422/52 |
| 2013/0171027 | A1* | 7/2013 | Serban | G01N 21/643 422/69 |

FOREIGN PATENT DOCUMENTS

DE    19839552 A1    7/2000

OTHER PUBLICATIONS

Carvajal MA., et al., "Hand-Held Optical Instrument for C02 in Gas Phase Based on Sensing Film Coating Optoelectronic Elements," Sensors and Actuators B, vol. 144, Jan. 29, 2010, pp. 232-238.
(Continued)

*Primary Examiner* — David P Porta
*Assistant Examiner* — Meenakshi S Sahu
(74) *Attorney, Agent, or Firm* — Slater Matsil, LLP

(57) ABSTRACT

A photonic gas sensor and a method for producing a photonic gas sensor are disclosed. In an embodiment a photonic gas sensor includes a component housing with at least one cavity, a radiation-emitting semiconductor chip arranged in the cavity and configured to transmit electromagnetic radiation in a first wavelength range, a radiation-detecting semiconductor chip arranged in the cavity and configured to detect electromagnetic radiation in a second wavelength range and an active sensor element having a fluorescent dye configured to emit electromagnetic radiation in the second wavelength range upon being excited by electromagnetic radiation in the first wavelength range, wherein an intensity
(Continued)

of the emitted electromagnetic radiation in the second wavelength range changes reversibly in presence of a gas to be detected.

19 Claims, 4 Drawing Sheets

(52) U.S. Cl.
CPC .............. *G01N 33/0054* (2013.01); *G01N 2021/6439* (2013.01); *G01N 2201/08* (2013.01)

(58) Field of Classification Search
CPC ....... G01N 2201/08; G01N 2021/6432; G01N 2021/773; G01N 2021/7786; G01N 2201/0221; G01N 2201/0222; G01N 21/643; G01N 31/223
See application file for complete search history.

(56) References Cited

OTHER PUBLICATIONS

G.R. McDowell, et al., "Towards a Novel Optical Trace Oxygen Sensor for Commercial Use," School of Engineering & Built Environment, Glasgow Caledonian University, Glasgow, UK, Oct. 30-Nov. 3, 2016, pp. 1-3.

* cited by examiner

PHOTONIC GAS SENSOR AND METHOD FOR PRODUCING A PHOTONIC GAS SENSOR

This patent application is a national phase filing under section 371 of PCT/EP2018/082390, filed Nov. 23, 2018, which claims the priority of German patent application 102017127671.8, filed Nov. 23, 2017, each of which is incorporated herein by reference in its entirety.

TECHNICAL FIELD

A photonic gas sensor and a method for producing a photonic gas sensor are specified.

BACKGROUND

A gas sensor is known, for example, from German Patent Application DE 19839552 A1.

SUMMARY

Embodiments provide an improved photonic gas sensor. In particular, a photonic gas sensor with a compact design will be specified. Further embodiments provide a method for producing an improved photonic gas sensor, in particular with a compact design.

According to an embodiment, the photonic gas sensor comprises a component housing with at least one cavity. The component housing can be an integral component housing, which is produced using a plastic molding process, such as an injection molding process, for example. Alternatively, the component housing can also be composed of a plurality of elements. For example, the component housing may be formed from a substrate, such as a ceramic plate or a printed circuit board (PCB), on which a frame is mounted. Side faces of the frame preferably form the side faces of the cavity.

According to another embodiment of the photonic gas sensor, a radiation-emitting semiconductor chip is arranged in the cavity of the component housing. The radiation-emitting semiconductor chip is preferably suitable for emitting electromagnetic radiation in a first wavelength range. The electromagnetic radiation in the first wavelength range is preferably emitted from a radiation emission surface of the radiation-emitting semiconductor chip.

The component housing has at least one cavity. For example, the component housing has a common cavity in which the radiation-emitting semiconductor chip and the radiation-detecting semiconductor chip are arranged. It is also possible that the component has two cavities, the radiation-emitting semiconductor chip being arranged in the first cavity and the radiation-detecting semiconductor chip in the second cavity.

According to one embodiment of the photonic gas sensor, the radiation-emitting semiconductor chip comprises an epitaxial semiconductor layer sequence with an active zone, in which the electromagnetic radiation in the first wavelength range is generated in the operation of the radiation-emitting semiconductor chip.

The radiation-emitting component is preferably a light-emitting diode chip.

The radiation-emitting semiconductor chip can be, for example, a so-called volume-emitting semiconductor chip or a thin-film semiconductor chip.

The volume-emitting semiconductor chip usually has a substrate on which the epitaxial semiconductor layer sequence has been epitaxially grown with the active zone. For example, the substrate may contain one of the following materials or may consist of one of the following materials: sapphire, silicon carbide. Volume-emitting semiconductor chips generally do not emit the electromagnetic radiation generated in the active via only one main surface, but also via side faces.

The thin-film semiconductor chip has an epitaxially grown semiconductor layer sequence that is applied to a different carrier than the growth substrate for the epitaxial semiconductor layer sequence. A mirror layer, which directs electromagnetic radiation from the active zone to a radiation emission surface, is particularly preferably arranged between the epitaxial semiconductor layer sequence and the carrier. The radiation emission area is usually comprised by a main surface of the thin-film semiconductor chip. Thin-film semiconductor chips generally do not emit the electromagnetic radiation which is generated in the active zone in operation, or only very slightly, via the side faces of the carrier, but have an essentially Lambertian radiation characteristic.

For example, the electromagnetic radiation in the first wavelength range, which is generated in the active zone, has ultraviolet radiation, infrared radiation, or visible light.

For example, the epitaxial semiconductor layer sequence is based on a nitride compound semiconductor material or is formed by a nitride compound semiconductor material. Nitride compound semiconductor materials are compound semiconductor materials that contain nitrogen, such as materials from the system $In_xAl_yGa_{1-x-y}N$ with $0 \leq x \leq 1$, $0 \leq y \leq 1$, and $x+y \leq 1$. If the epitaxial semiconductor layer sequence, and in particular the active zone, is based on a nitride compound semiconductor material, then the active zone is generally suitable for generating electromagnetic radiation from the ultraviolet to the blue-green spectral range.

It is also possible that the epitaxial semiconductor layer sequence is based on a phosphide compound semiconductor material or is formed from a phosphide compound semiconductor material. Phosphide compound semiconductor materials are compound semiconductor materials that contain phosphorus, such as materials from the system $In_xAl_yGa_{1-x-y}P$ with $0 \leq x \leq 1$, $0 \leq y \leq 1$, and $x+y \leq 1$. If the epitaxial semiconductor layer sequence, and in particular the active zone, is based on a phosphide compound semiconductor material, then the active zone is generally suitable for generating electromagnetic radiation from the green to the red spectral range.

Finally, it is possible that the epitaxial semiconductor layer sequence is based on an arsenide compound semiconductor material or is formed from an arsenide compound semiconductor material. Arsenide compound semiconductor materials are compound semiconductor materials that contain arsenic, such as materials from the system $In_xAl_yGa_{1-x-y}As$ with $0 \leq x \leq 1$, $0 \leq y \leq 1$, and $x+y \leq 1$. If the epitaxial semiconductor layer sequence, and in particular the active zone, is based on an arsenide compound semiconductor material, then the active zone is generally suitable for generating electromagnetic radiation from the red to the infrared spectral range.

According to a further embodiment of the photonic gas sensor, this comprises a radiation-detecting semiconductor chip. The radiation-detecting semiconductor chip is preferably arranged in the cavity and is suitable for detecting electromagnetic radiation in a second wavelength range. The first wavelength range is preferably different from the second wavelength range. In particular, the second wavelength range preferably comprises longer wavelengths than the first wavelength range. The radiation-detecting semiconductor chip is preferably a photodiode chip. The photodiode chip can be based on silicon.

According to another embodiment, the photonic gas sensor comprises an active sensor element, which is suitable for detecting electromagnetic radiation in the second wavelength range. The active sensor element preferably has a fluorescent dye, which upon being excited by electromagnetic radiation in the first wavelength range emits electromagnetic radiation in the second wavelength range.

The fluorescent dye in this case is preferably designed to be wavelength-converting. In particular, the term "wavelength-converting" in this case is used, in particular, to mean that incident electromagnetic radiation in a first wavelength range is converted into electromagnetic radiation in a second wavelength range, preferably of longer wavelength. As a rule, a wavelength-converting element absorbs electromagnetic radiation in the first wavelength range, converts it into electromagnetic radiation in the second wavelength range via electronic processes at the atomic and/or molecular level, and then retransmits the converted electromagnetic radiation. In particular, pure scattering or pure absorption is not understood as wavelength-converting.

The fluorescent dye is preferably designed such that the intensity of the emitted electromagnetic radiation in the second wavelength range is reversibly modified, for example, reduced, in the presence of a gas to be detected. In other words, the intensity of the electromagnetic radiation in the second wavelength emitted by the fluorescent dye changes when the gas to be detected is in direct contact with the fluorescent dye and returns to its original state when the gas is removed.

In the case of the present photonic gas sensor the fluorescent dye is thus used to detect the gas. The fluorescent dye is designed in such a way that the intensity of the electromagnetic radiation emitted by the dye changes, for example reduces, in a reversible manner in the presence of the gas to be detected. The radiation-detecting semiconductor chip is designed and arranged to detect the intensity of the electromagnetic radiation of the second wavelength range emitted by the fluorescent dye of the active sensor element, thereby capturing the change in the intensity of the electromagnetic radiation of the fluorescent dye in the presence of the gas to be detected.

For example, it is possible that the phase shift of the electromagnetic radiation emitted by the active sensor element under intensity modulated excitation is measured.

In the present case only the intensity of the electromagnetic radiation of the second wavelength range emitted by the active sensor element is preferably measured. This may advantageously be sufficient, due to the fixed position between the radiation-emitting semiconductor chip and the radiation-detecting semiconductor chip. This allows the use of simple electronics.

For example, the gas to be detected can be oxygen ($O_2$), carbon dioxide ($CO_2$), nitrogen dioxide ($NO_2$), carbon monoxide (CO), ammonia ($NH_3$), or a mixture of at least two of these gases.

For example, the fluorescent dye can be a fluorescein, a rhodamine, a cyanine, a coumarine, a fluorescent polymer, a fluorescent metal-ion complex, or nanoparticles. In addition to fluoresceins, rhodamines, cyanines and coumarines, other organic fluorescent dyes may be suitable for use in the photonic gas sensor.

For example, a fluorescent metal-ion complex may have europium(III) ions ($EU^{3+}$) and/or terbium(III) ions ($Tb^{3+}$) as metal ions. For detecting oxygen, Tris(2.2'-bipyridyl/dichlororuthenium (II) hexahydrate (Ru(bpy)32+) may be suitable, for example. Carboxynaphtofluorescein (CNF), for example, can be used for detecting carbon dioxide, while a fluorescein or coumarine may be suitable for detecting ammonia. Suitable materials for the fluorescent dye are described, for example, in the publication Bhopate et al., Journal of Nanomed Nanotechnology 2017, 8.2 (DOI 10.4172/2157-7439.1000436), the relevant contents of which are incorporated by reference.

According to a further embodiment of the photonic gas sensor, the active sensor element comprises a polymer matrix. The fluorescent dye of the active sensor element is preferably embedded in the polymer matrix. Furthermore, the polymer matrix is preferably permeable to the gas to be detected. For example, the polymer matrix is a silicone or a polysilazane. In addition, other polymers may be suitable as the polymer matrix as long as they are permeable to the gas to be detected. For example, the polymer matrix can be made of a polymer that can be cured thermally or by UV radiation.

According to a further embodiment of the photonic gas sensor, the active sensor element is implemented as a sensitive casting. Preferably, at least the radiation-emitting semiconductor chip is embedded in the sensitive casting. For example, the sensitive casting completely fills the first cavity, in which the radiation-emitting semiconductor chip is arranged, or the second cavity, in which the radiation-detecting semiconductor chip is arranged. Furthermore, it is also possible that the sensitive casting encloses the radiation-emitting semiconductor chip or the radiation-detecting semiconductor chip in a hemispherical shape. The sensitive casting may be formed by the polymer matrix containing the embedded fluorescent dye that these two materials comprise.

It is also possible that both the radiation-emitting semiconductor chip and the radiation-detecting semiconductor chip are enveloped by the sensitive casting. In this case, the radiation-emitting semiconductor chip and the radiation-detecting semiconductor chip are preferably arranged in a common cavity of the component housing. In this embodiment, the sensitive casting envelops the radiation-emitting semiconductor chip and the radiation-detecting semiconductor chip, particularly preferably completely. The sensitive casting preferably fills the common cavity, preferably completely.

It is also possible for the component housing to have two cavities separated from each other. For example, the component housing has a first cavity and a second cavity separated from each other, for example by a partition wall. Preferably, the radiation-detecting semiconductor chip is arranged in the first cavity and the radiation-emitting semiconductor chip is arranged in the second cavity. In this embodiment, the active sensor element is preferably implemented as a sensitive casting in the second cavity. The sensitive casting in this case envelops the radiation-emitting semiconductor chip, particularly preferably completely.

It is also possible that the active sensor element is implemented as a sensitive layer. In this case, the main extension plane of the sensitive layer is arranged parallel to a radiation emission surface of the radiating-emitting semiconductor chip and/or parallel to a radiation entry surface of the radiation-detecting semiconductor chip. For example, the active sensitive layer comprises the polymer matrix into which the fluorescent dye is embedded, or is formed by these materials.

In this case the sensitive active layer is preferably applied to a transparent carrier element. In particular, the carrier element is preferably transparent to electromagnetic radiation in the first wavelength range and electromagnetic radiation in the second wavelength range. The sensitive layer is particularly preferably applied over the whole surface of the transparent carrier element. The transparent carrier element preferably acts as a waveguide layer, which injects the electromagnetic radiation of the second wavelength range and transports it laterally to the detecting semiconductor chip.

The transparent carrier element preferably faces the radiation-emitting semiconductor chip and the radiation-detecting semiconductor chip and is preferably permeable to the gas to be detected.

According to another embodiment the photonic gas sensor comprises a filter that filters electromagnetic radiation in the first wavelength range. This increases the sensitivity of the photonic gas sensor. For example, the filter can be implemented as a bandpass filter that only filters out electromagnetic radiation of the first wavelength range, or as a long-pass filter in which an upper edge of the filter coincides with the upper edge of the first wavelength range. In other words, the long-pass filter preferably filters out electromagnetic radiation with wavelengths less than the longest wavelength of the first wavelength range and transmits electromagnetic radiation with wavelengths greater than the longest wavelength of the first wavelength range. The filter is particularly preferably designed to be permeable to the gas to be detected.

For example, the filter can be designed as a dichroic filter. For example, dichroic layers can be applied to a small plate, such as a small glass plate, wherein these elements form the filter. It is also possible that the filter may have color pigments that absorb the electromagnetic radiation to be filtered. For example, the color pigments can also be embedded in a polymer matrix material such as silicone. The color pigments can be organic materials. In contrast to the fluorescent dye, the color pigments are preferably not designed to be wavelength-converting, rather they absorb a specific spectral component from incident external light, so that the spectral range of the remaining visible light determines the color of the color pigments.

According to one embodiment of the photonic gas sensor, the filter is formed as a filtering layer and is applied to the radiation entry surface of the radiation-detecting semiconductor chip. For example, as described above, the filter may be formed by dichroic layers on a small glass plate. For example, the filtering layer can be glued onto the radiation entry surface of the radiation-detecting semiconductor chip.

According to one embodiment of the photonic gas sensor, the sensor element is formed as a sensitive layer and the filter element as a filtering layer. In this case, the filtering layer is preferably arranged between the radiation entry surface of the radiation-detecting semiconductor chip and the sensitive layer.

It is also possible that the filter is formed as a filtering casting. In this case, the radiation-detecting semiconductor chip is preferably embedded in the filtering casting. For example, the radiation-detecting semiconductor chip is inserted into a cavity of the component housing and the cavity is completely filled, for example, with the filtering casting. The filtering casting is formed, for example, by a polymer matrix material with color pigments. The filtering casting can be produced by dispensing or jetting in droplet form.

According to another embodiment of the photonic gas sensor, side faces of the radiation-detecting semiconductor chip are coated with a protective layer that prevents electromagnetic radiation from being injected laterally into the radiation-detecting semiconductor chip. The protective layer can be designed, for example, to be reflecting. For example, the protective layer comprises a silicone, into which reflective particles, such as titanium dioxide particles, are introduced.

According to a further embodiment, the photonic gas sensor comprises a covering element. The covering element is preferably designed to be absorbent or reflecting, at least for the electromagnetic radiation in the first wavelength range. The covering element is preferably arranged within the photonic gas sensor in such a way that it prevents external electromagnetic radiation, such as sunlight, from entering the photonic gas sensor and, in particular, from reaching the fluorescent dye. In this way, bleaching of the dye can at least be reduced. Bleaching of the dye involves an irreversible decrease in the intensity of the electromagnetic radiation emitted by the dye, for example due to degradation of the fluorescent dye. In addition, the covering element is preferably permeable to the gas to be detected. It is also possible that a breakthrough that preferably completely penetrates the covering element is arranged in the covering element. The gas to be detected advantageously penetrates the breakthrough to reach the sensor element. The breakthrough is preferably a drilled hole, for example.

The covering element, which is designed to be absorbent for the electromagnetic radiation in the first wavelength range, may comprise a silicone, for example, into which black pigment particles, such as soot particles, are embedded. In this case, the silicone is preferably permeable to the gas to be detected.

For example, a covering element that is designed to be reflective at least for the electromagnetic radiation of the first wavelength range can be made of a polymer, such as a silicone, into which reflecting particles are introduced. The reflecting particles can be titanium dioxide particles, for example. Such a covering element is designed, in particular, to be diffusely reflecting. The diffusely reflecting covering element usually shows a white color percept.

According to a preferred embodiment of the photonic gas sensor, the covering element is arranged between an external surface of the photonic gas sensor and the sensor element. For example, a main surface of the covering element forms the outer surface of the photonic gas sensor.

According to another embodiment, the photonic gas sensor comprises a waveguide layer that directs electromagnetic radiation of the second wavelength range to the radiation-detecting semiconductor chip. Preferably, electromagnetic radiation, emitted by the sensor element, in the second wavelength range is coupled into the waveguide layer so that the latter can direct the electromagnetic radiation in the second wavelength range to the radiation-detecting semiconductor chip. The waveguide layer is particularly advantageous if the radiation-generating semiconductor chip and the radiation-detecting semiconductor chip are arranged in separate cavities.

The waveguide layer can be, for example, the transparent carrier element of the sensitive element already described above. It is also possible that the photonic gas sensor comprises a further waveguide layer, produced and arranged separately from the sensitive layer. The waveguide layer is also particularly preferably designed to be permeable to the gas to be detected.

For example, the waveguide layer is formed of a transparent casting compound, such as a silicone, in which a large number of scattering particles are applied. The transparent casting compound can be a silicone, for example. It is also possible that the waveguide layer can contain or consist of one of the following materials: glass, epoxy resin, polymethyl methacrylate.

The waveguide layer is preferably provided with coupling structures on a main surface that faces toward the radiation emission surface of the radiation-emitting semiconductor chip and/or toward the radiation entry surface of the radiation-detecting semiconductor chip. The coupling structures are suitable for increasing the coupling and/or the decoupling of electromagnetic radiation into and out of the waveguide layer. The coupling structures can be arranged evenly over the main surface of the covering element or only in certain regions of the main surface, e.g., over the radiation-emitting semiconductor chip and/or the radiation-detecting semiconductor chip.

According to an embodiment of a method for producing a photonic gas sensor, a radiation-emitting semiconductor chip and a radiation-detecting semiconductor chip are arranged on a mounting surface of a substrate. For example, the radiation-emitting semiconductor chip and the radiation-detecting semiconductor chip are arranged on a common mounting surface of a common substrate. The substrate can be a ceramic plate or a printed circuit board, for example.

According to another embodiment of the method, a frame is mounted on the substrate, so that the substrate and the frame form the component housing with the cavity.

According to a further embodiment of the method, an active sensitive layer is arranged on and fastened to the frame as a sensor element.

All the embodiments and features described in connection with the photonic gas sensor can also be implemented in the method, and vice versa.

The present photonic gas sensor is based, among other things, on the idea of using a fluorescent dye in order to detect a gas. The fluorescent dye is suitable for modifying, for example reducing, in a reversible manner the intensity of the electromagnetic radiation that it emits in the presence of the gas to be detected.

In addition, the elements of the photonic gas sensor described here, such as the radiation-emitting semiconductor chip and the radiation-detecting semiconductor chip, must be arranged in a common component housing. This advantageously enables the most compact design of the photonic gas sensor. The component housing in this case is particularly preferably a component housing such as is already used in light-emitting diode technology, for example. This can be an integrally designed, prefabricated component housing with one or more cavities. It is also possible that the component housing is composed of different elements, such as a substrate and a frame.

The gas is preferably detected in this case by means of the fluorescent dye, which is preferably embedded in a polymer matrix that can preferably also be used as a casting material of an LED. This simplifies the production of the photonic gas sensor.

The photonic gas sensor is particularly preferably suitable for mounting in an SMT assembly process (SMT: Surface Mounting Technology), such as a pick-and-place process, SAC solder paste, and reflow soldering using an SAC solder paste. This advantageous effect is possible especially when using a temperature-stable polymer matrix, such as silicone. However, it is also possible to use other connecting elements to assemble the photonic gas sensor, such as Anisotropic Conductive Paste (ACP), Anisotropic Conductive Film (ACF), or low-melting-point solders. Advantageously, these assembly processes are, in particular, comparatively cheap.

Due to its small dimensions, the photonic gas sensor is particularly suitable for use in applications where space is limited, such as in a mobile phone or in clothing.

BRIEF DESCRIPTION OF THE DRAWINGS

Further advantageous embodiments and further developments of the invention arise from the exemplary embodiments, described hereafter in connection with the figures.

The schematic cross-sectional drawings of FIGS. 1, 2, 4, 5 and 6 show a photonic gas sensor according to a different exemplary embodiment in each case.

Using the schematic cross-sectional drawings of FIGS. 7 to 10, a method for producing a photonic gas sensor is explained in more detail.

Identical, similar or equivalently functioning elements are labelled with the same reference sign in the figures. The figures and the relative proportions of the elements represented in the figures are not to be considered to be true to scale. Instead, individual elements, especially layer thicknesses, can be shown exaggerated in size and/or for better visualization and/or better understanding.

DETAILED DESCRIPTION OF ILLUSTRATIVE EMBODIMENTS

Figure 1:
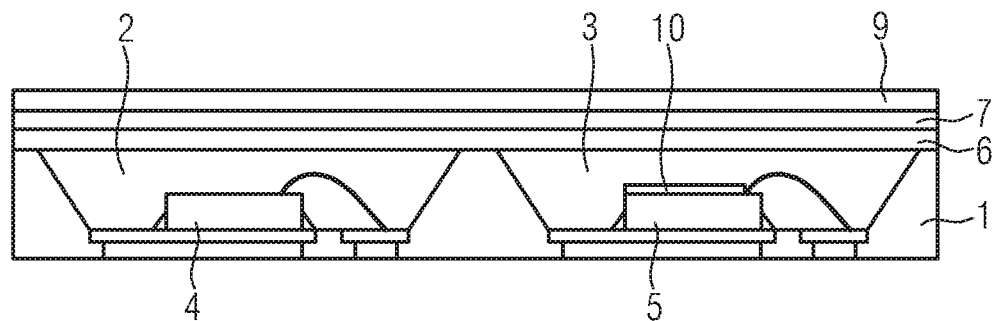

The photonic gas sensor, as shown in the exemplary embodiment of FIG. 1, has a component housing 1 with two cavities 2, 3 separated from each other. The component housing 1 in this case is a pre-fabricated component housing 1 in which a conductor frame is embedded in a plastic body.

In the first cavity 2, a radiation-emitting semiconductor chip 4 is arranged, which emits electromagnetic radiation in a first wavelength range from a radiation emission surface. In the second cavity 3, a radiation-detecting semiconductor chip 5 is arranged, which is suitable for detecting electromagnetic radiation in a second wavelength range that enters the radiation-detecting semiconductor chip 5 through a radiation entry surface. The radiation emission surface of the radiation-emitting semiconductor chip 4 and the radiation entry surface of the radiation-detecting semiconductor chip 5 are arranged parallel to a main surface of the photonic gas sensor. The radiation-emitting semiconductor chip 4 can be a volume-emitting semiconductor chip or a surface-emitting semiconductor chip. The radiation-detecting semiconductor chip 5 in this case is a photodiode, particularly preferably a silicon-based photodiode.

The first cavity 2 and the second cavity 3 of the component housing 1 are in this case completely covered by a waveguide layer 6. For example, the waveguide layer 6 may comprise glass or a polymer, or be formed of one of these materials. The waveguide layer 6 is particularly preferably permeable at least to electromagnetic radiation in the first wavelength range and/or electromagnetic radiation in the second wavelength range.

Figure 3:
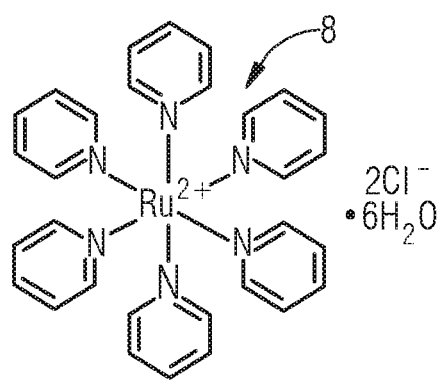
FIG. 3 shows a chemical structural formula of a fluorescent dye for a photonic gas sensor according to one exemplary embodiment.

In addition, the gas sensor according to FIG. 1 comprises an active sensor element 7, which in the present case is formed as an active sensitive layer. The active sensitive layer in this case is applied in direct contact with the waveguide layer 6. The active sensitive layer 7 comprises a silicone as a polymer matrix, into which a fluorescent dye 8 is introduced. The fluorescent dye 8 can be Tris(2.2'-bipyridyl)

dichlororuthenium(II) hexahydrate, for example. An example of the chemical structure formula of this fluorescent dye 8 is illustrated in FIG. 3.

The fluorescent dye 8 is suitable for detecting oxygen. In the presence of oxygen, the intensity of the electromagnetic radiation of the second wavelength range emitted by the fluorescent dye 8 decreases in a reversible manner.

On the active sensitive layer 7, a reflective covering element 9 is applied in direct contact with it. The reflective covering element 9 comprises silicone as a polymer matrix. Reflective particles such as titanium dioxide particles are embedded in the polymer matrix. Alternatively, the covering element 9 may be black, for example by introducing soot particles into the silicone as a polymer matrix.

In the operation of the photonic gas sensor, the radiation-emitting semiconductor chip 4 emits electromagnetic radiation in the first wavelength range from its radiation emission surface. The electromagnetic radiation in the first wavelength range strikes the waveguide layer 6 and is coupled into the active sensitive layer 7 by the waveguide layer 6. There, the electromagnetic radiation in the first wavelength range excites the fluorescent dye 8 so that the dye emits electromagnetic radiation in a second, longer wavelength range. Electromagnetic radiation in the second wavelength range is transported by the waveguide layer 6 to the second cavity 3, where the radiation-detecting semiconductor chip 5 is arranged. The radiation-detecting semiconductor chip 5 is suitable for detecting electromagnetic radiation in the second wavelength range. If oxygen is now present in the sensitive active layer 7 as the gas to be detected, the intensity of the electromagnetic radiation of the second wavelength range emitted by the fluorescent dye 8 is reduced. The reduction in intensity is detected by the radiation-detecting semiconductor chip 5, so that the presence of oxygen can be detected.

The covering element 9, which can be designed to be reflective, for example white, or absorbent, for example black, prevents any bleaching of the fluorescent dye 8, i.e., an irreversible degradation of the fluorescent dye 8, which can lead to an irreversible reduction in the intensity of the electromagnetic radiation of the second wavelength range emitted by the fluorescent dye 8.

The photonic gas sensor preferably has a dichroic filter 10, which is placed upstream of the radiation entry surface of the radiation-detecting semiconductor chip 5 in a direction of incoming radiation. For example, the dichroic filter 10 can cover the second cavity 3 or else it can be arranged on the radiation entry surface of the radiation-detecting semiconductor chip 5, for example by adhesive bonding. The dichroic filter 10 improves the sensitivity of the photonic gas sensor.

Figure 2:
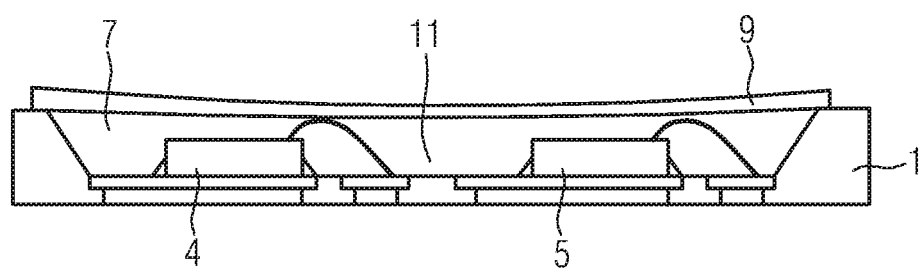

Unlike the photonic gas sensor according to the exemplary embodiment of FIG. 1, the photonic gas sensor according to the exemplary embodiment of FIG. 2 has a single common cavity 11, in which the radiation-emitting semiconductor chip 4 and the radiation-detecting semiconductor chip 5 are arranged. In this exemplary embodiment, a sensitive casting that completely fills the cavity is used as the active sensor element 7. The active sensitive casting 7 comprises silicone as a polymer matrix, into which the fluorescent dye 8 is embedded. The cavity 11 is completely covered with the covering element 9.

Figure 4:
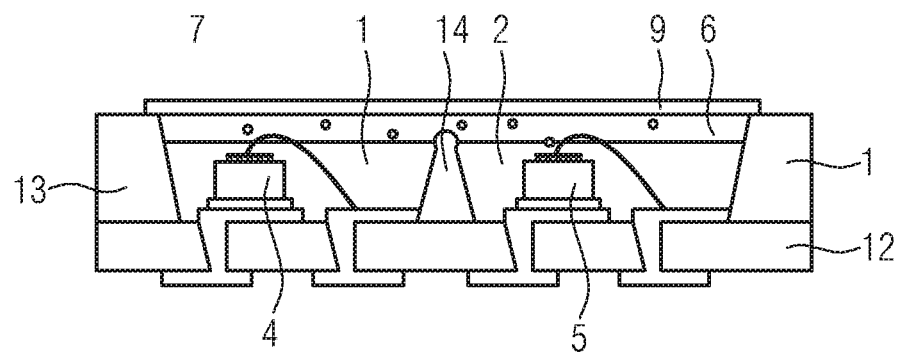

In the same way as the photonic gas sensor according to the exemplary embodiment of FIG. 4, the photonic gas sensor according to the exemplary embodiment of FIG. 4 has a component housing with two separate cavities 2, 3, wherein a radiation-emitting semiconductor chip 4 is arranged in the first cavity 2 and a radiation-detecting semiconductor chip 5 is arranged in the second cavity 3. The component housing 1 consists in this case of a substrate 12, such as a printed circuit board or a ceramic plate, on which a frame 13 is mounted. Furthermore, the first cavity 2 and the second cavity 3 are separated by a partition wall 14, which like the frame 13 is mounted on the substrate 12. The frame 13 in this case is designed to be reflecting. For example, the frame 13 is made of a silicone with titanium dioxide particles.

In the first cavity 2, an active sensor element 7 is arranged, which in this case is formed as an active sensitive casting. The active sensitive casting 7 comprises a silicone as a polymer matrix, into which a fluorescent dye 8 is introduced. The active sensitive casting 7 in this case completely envelops the radiation-emitting semiconductor chip 4.

In the second cavity 3, in which the radiation-detecting semiconductor chip 5 is arranged, a filter 10 is additionally arranged, which is formed as a filtering casting. The filtering casting 10 is a silicone into which the color pigments of an organic color filter are incorporated. The filter 10 is suitable for absorbing electromagnetic radiation in the first wavelength range emitted by the radiation-emitting semiconductor chip 4. This increases the sensitivity of the photonic gas sensor.

In addition, the photonic gas sensor according to the exemplary embodiment of FIG. 4 comprises a waveguide layer 6 which covers the two cavities 2, 3 and is suitable for directing electromagnetic radiation of the second wavelength range, emitted by the active sensitive casting 7, laterally to the second cavity 3 and the radiation-detecting semiconductor chip 5. The waveguide layer 6 in this case is made of a silicone in which scattering particles are introduced.

A covering element 9 is applied to the waveguide layer 6, which in the present case is designed to be reflective. The covering element 9 is made of a silicone into which titanium dioxide particles are introduced.

Figure 5:
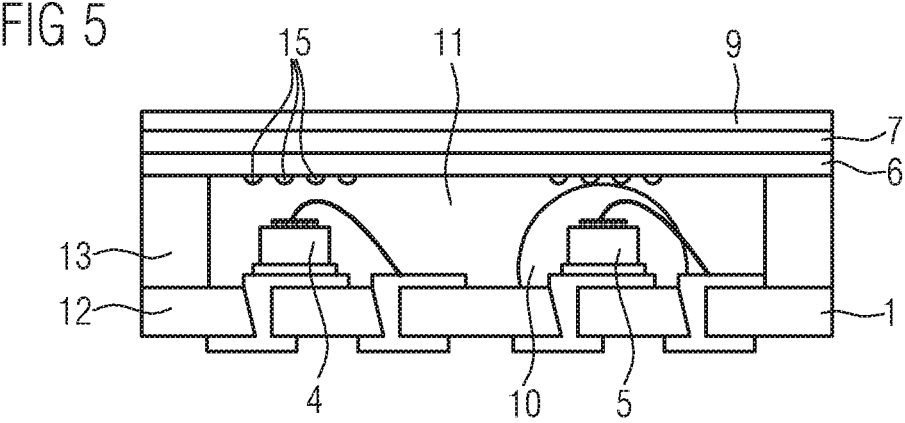

In the case of the photonic gas sensor according to the exemplary embodiment of FIG. 5, the component housing 1 also comprises a substrate 12, such as a printed circuit board or a ceramic substrate, on which a frame 13 is mounted. The frame 13 here forms the side walls of a common cavity 11, into which the radiation-emitting semiconductor chip 4 and the radiation-detecting semiconductor chip 5 are inserted. For example, the frame 13 can be glued to the printed circuit board or the ceramic substrate.

The radiation-detecting semiconductor chip 5 is surrounded by a filter 10. The filter 10 comprises a polymer matrix such as a silicone, into which organic color pigments are incorporated as color filters which absorb electromagnetic radiation in the first wavelength range. The filter 10 is designed in this case as a filtering casting, which can be applied by dispensing, for example. The filtering casting 10 forms a hemispherical shape and completely embeds the radiation-detecting semiconductor chip 5. However, the filtering casting 10 does not completely fill the cavity 11. The filtering casting 10 is designed in this case in the shape of a lens.

In addition, the photonic gas sensor according to the exemplary embodiment of FIG. 5 comprises the waveguide layer 6, the active sensitive layer 7 and the covering element 9. The active sensitive layer 7 in this case is arranged between the waveguide layer 6 and the covering element 9, wherein the waveguide layer 6 faces towards the cavity 11 of the component housing 1 and the covering element 9 faces towards an outer surface of the photonic gas sensor.

Coupling structures 15 are arranged on a main surface of the waveguide layer 6, which are suitable for coupling in or decoupling electromagnetic radiation in the first wavelength range and/or the second wavelength range. The coupling structures 15 face the cavity 11 of the photonic gas sensor.

Figure 6:
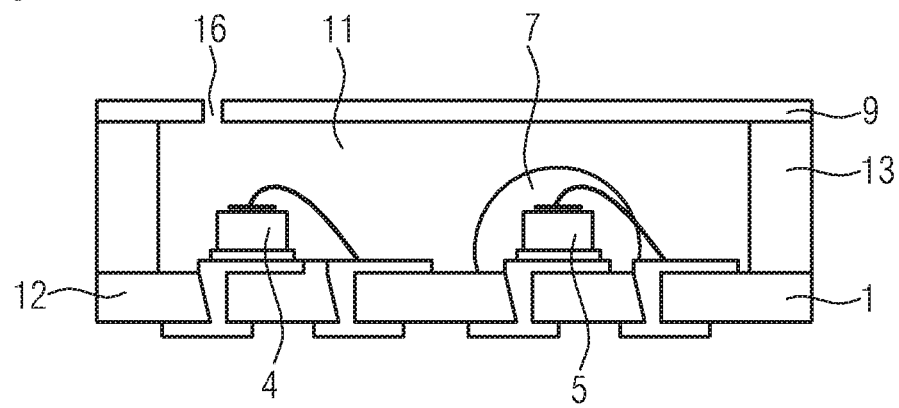

In the photonic gas sensor according to the exemplary embodiment of FIG. 6, a breakthrough 16, such as a drilled hole, is provided in the covering element 9. The breakthrough 16 completely penetrates the covering element 9. This allows the gas to be detected to be transported into the cavity 11. In this exemplary embodiment, the active sensor element 7 is formed as a semi-circular sensitive casting, which completely envelops the radiation-detecting semiconductor chip 5, but leaves areas of the cavity 11 exposed. In this case, it is possible that a reflective casting, for example titanium dioxide in a polymer matrix such as silicon, is applied to side faces of the detecting semiconductor chip 5, in order to protect the radiation-detecting semiconductor chip from electromagnetic radiation being coupled in laterally. The photonic gas sensor as shown in the exemplary embodiment of FIG. 6 can also comprise a filter 10, for example a dichroic, filtering layer, which is applied to the radiation entry surface of the radiation-detecting semiconductor chip 5. The filter 10 can also be designed as a filtering casting.

Figure 7:
Figure 8:
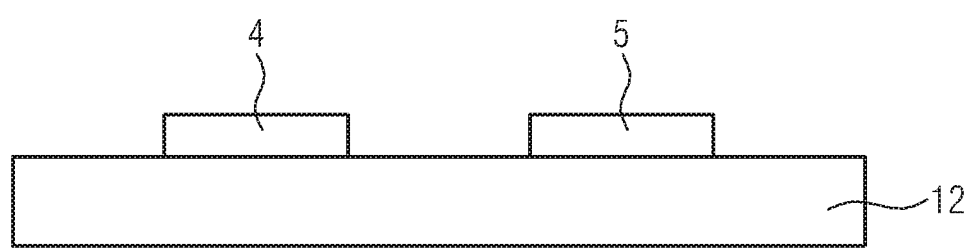
Figure 9:
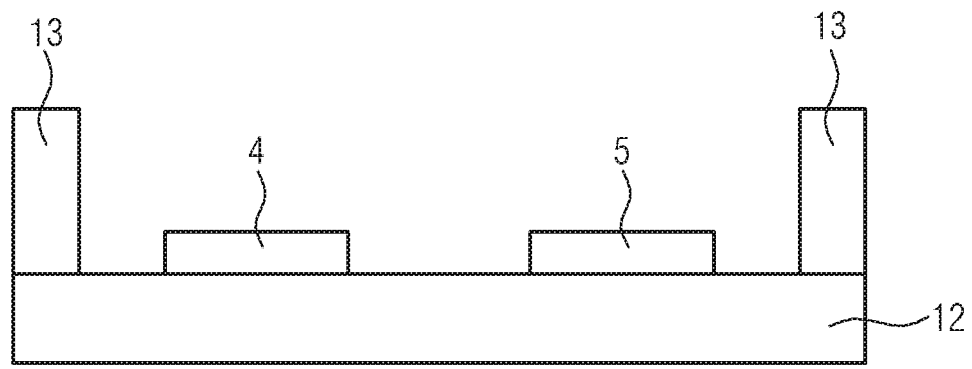
Figure 10:
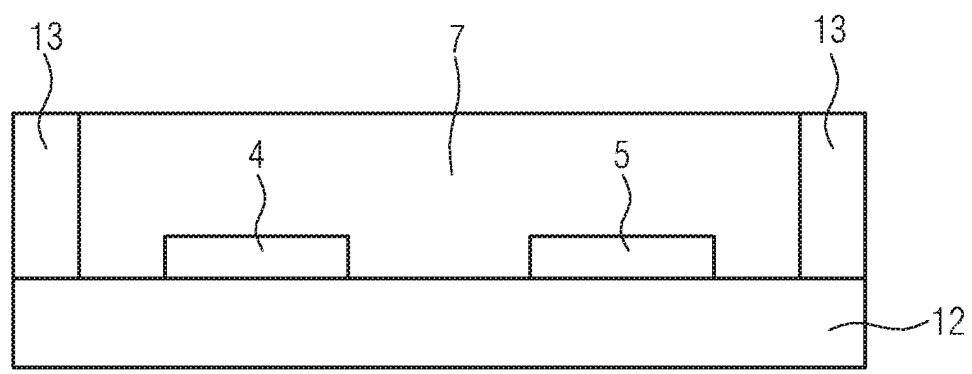

In the method according to FIGS. 7 to 10, a substrate 12 is first provided. For example, the substrate 12 can be a printed circuit board or a ceramic substrate (FIG. 7). A radiation-emitting semiconductor chip 4 and a radiation-detecting semiconductor chip 5 are mounted on a mounting surface of the substrate 12 (FIG. 8). Then, a frame 13 is mounted on the substrate 12, so that a cavity 11 is formed from the frame 13 and the substrate 12, in which the radiation-emitting semiconductor chip 4 and the radiation-detecting semiconductor chip 5 are arranged (FIG. 9). In a next step, an active sensor element 7, which in this case is formed as an active sensitive casting, is filled into the cavity 11 (FIG. 10).

The invention is not limited to the embodiments by the fact that the description is based on them. Rather, the invention comprises each new feature, as well as any combination of features, which includes in particular every combination of features in the patent claims, even if this feature or this combination itself is not explicitly specified in the patent claims or exemplary embodiments.

The invention claimed is:

1. A photonic gas sensor comprising:
a component housing with a first cavity and a second cavity separated from each other;
a radiation-emitting semiconductor chip arranged in the first cavity and configured to transmit electromagnetic radiation in a first wavelength range;
a radiation-detecting semiconductor chip arranged in the second cavity and configured to detect electromagnetic radiation in a second wavelength range;
an active sensor element formed as a sensitive casting in the first cavity and having a fluorescent dye configured to emit electromagnetic radiation in the second wavelength range upon being excited by the electromagnetic radiation in the first wavelength range; and
a waveguide layer configured to direct the electromagnetic radiation in the second wavelength range to the radiation-detecting semiconductor chip,
wherein an intensity of the emitted electromagnetic radiation in the second wavelength range changes reversibly in presence of a gas to be detected.

2. The photonic gas sensor of claim 1, wherein the active sensor element comprises a polymer matrix in which the fluorescent dye is embedded and which is permeable to the gas to be detected.

3. The photonic gas sensor of claim 2, wherein the sensitive casting embeds at least the radiation-emitting semiconductor chip.

4. The photonic gas sensor of claim 1, wherein the active sensor element is formed as a sensitive layer, a main extension plane of the sensitive layer being located parallel to a radiation emission surface of the radiation-emitting semiconductor chip and/or parallel to a radiation entry surface of the radiation-detecting semiconductor chip.

5. The photonic gas sensor of claim 4,
wherein the sensitive layer comprises a polymer matrix in which the fluorescent dye is embedded, and
wherein the sensitive layer is attached to a transparent carrier element.

6. The photonic gas sensor of claim 1, further comprising a filter configured to filter out the electromagnetic radiation of the first wavelength range.

7. The photonic gas sensor of claim 6, wherein the filter is formed as a filtering layer and is attached to a radiation entry surface of the radiation-detecting semiconductor chip.

8. The photonic gas sensor of claim 1, wherein the active sensor element is formed as a sensitive layer and a filter element as a filtering layer, and wherein the filtering layer is arranged between a radiation entry surface of the radiation-detecting semiconductor chip and the sensitive layer.

9. The photonic gas sensor of claim 8, wherein the filter element is formed as a filtering casting in which the radiation-detecting semiconductor chip is embedded.

10. The photonic gas sensor of claim 1, further comprising a covering element configured to be absorbent or reflective at least for the electromagnetic radiation in the first wavelength range.

11. The photonic gas sensor of claim 10, wherein the covering element is arranged between an outer surface of the photonic gas sensor and the active sensor element.

12. The photonic gas sensor of claim 1, wherein the waveguide layer has a transparent casting compound into which a plurality of scattering particles is incorporated.

13. The photonic gas sensor of claim 1, wherein the waveguide layer comprises glass.

14. The photonic gas sensor of claim 1, wherein, on a main surface facing a radiation emission surface of the radiation-emitting semiconductor chip and/or a radiation entry surface of the radiation-detecting semiconductor chip, the waveguide layer has coupling structures configured to increase coupling and/or decoupling of electromagnetic radiation into or out of the waveguide layer.

15. The photonic gas sensor of claim 1, wherein the fluorescent dye comprises a fluorescein, a rhodamine, a cyanine, a coumarin, a fluorescent polymer, a fluorescent metal-ion complex or nanoparticles.

16. A method for producing the photonic gas sensor of claim 1, the method comprising:
arranging the radiation-emitting semiconductor chip and the radiation-detecting semiconductor chip on a mounting surface of a substrate;
mounting a frame on the substrate so that the substrate and the frame form the component housing with the first and second cavities; and
arranging an active sensitive layer on the frame as the active sensor element.

17. The method of claim 16, wherein the substrate is based on a ceramic or is a printed circuit board.

18. The photonic gas sensor of claim 1, wherein the waveguide layer comprises epoxy resin.

19. The photonic gas sensor of claim 1, wherein the waveguide layer comprises polymethyl methacrylate.

* * * * *